United States Patent [19]

Brennan

[11] Patent Number: 5,320,215

[45] Date of Patent: Jun. 14, 1994

[54] VIAL DISPENSING CARTON

[76] Inventor: V. Jack Brennan, 2850 Lombardy Rd., San Marino, Calif. 91108

[21] Appl. No.: 45,377

[22] Filed: Apr. 9, 1993

[51] Int. Cl.⁵ .............................................. B65D 81/36
[52] U.S. Cl. .............................. 206/44.120; 206/443; 206/526; 220/403; 229/221; 221/302; 221/305
[58] Field of Search ............... 206/44.12, 427, 443, 206/526, 528; 220/403; 229/162, 221, 210; 221/64, 103, 133, 302, 305

[56] References Cited

U.S. PATENT DOCUMENTS

| | | | |
|---|---|---|---|
| 2,022,906 | 12/1935 | Weeks | 229/162 |
| 2,706,066 | 4/1955 | Wells | 221/305 |
| 2,933,229 | 4/1960 | Bensel | 220/403 |
| 3,858,717 | 1/1975 | Peters | 206/44.12 |
| 4,186,866 | 2/1980 | Zicko | 229/162 |
| 4,318,052 | 2/1979 | Torigian | 229/221 |
| 4,715,511 | 12/1987 | Bahlen | 220/403 |
| 4,838,424 | 6/1989 | Petzelt | 229/221 |
| 4,863,052 | 9/1989 | Lambert | 220/403 |
| 5,048,691 | 9/1991 | Heuberger et al. | 229/162 |

FOREIGN PATENT DOCUMENTS 251103  1/1988  European Pat. Off. ............ 221/302

*Primary Examiner*—David T. Fidei
*Attorney, Agent, or Firm*—Fitch, Even, Tabin & Flannery

[57] ABSTRACT

An inventory of pharmaceutical vials is kept in an inexpensive manner by providing a plurality of stackable cartons stacked in a neat array and each having a front access panel which opens to form an access window to allow access to remove vials from the interior of one of the respective cartons. The cartons having indicia indicating the type and size of vials stored therein. The preferred cartons are in the shape of a box having a hinged access panel die cut into the carton providing an access window or opening on its face. The window allows access by hand into the contents of a plastic bag within the carton. When the access panel is open, portions of the plastic bag may be draped out from the opening to allow easy access to the contents of the bag. The plastic bag and its contents are originally placed within the carton through end flaps located either adjacent or opposite the face of a carton. Upon placing the contents into the carton, the top end flaps may be closed and permanently sealed. The carton thus serves several functions including shipping, storage and inventory.

13 Claims, 1 Drawing Sheet

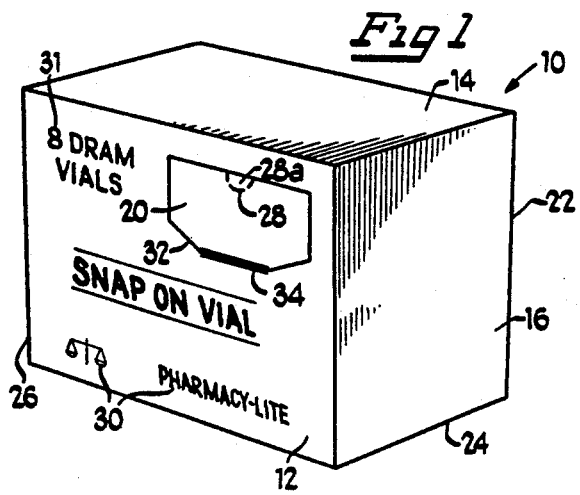
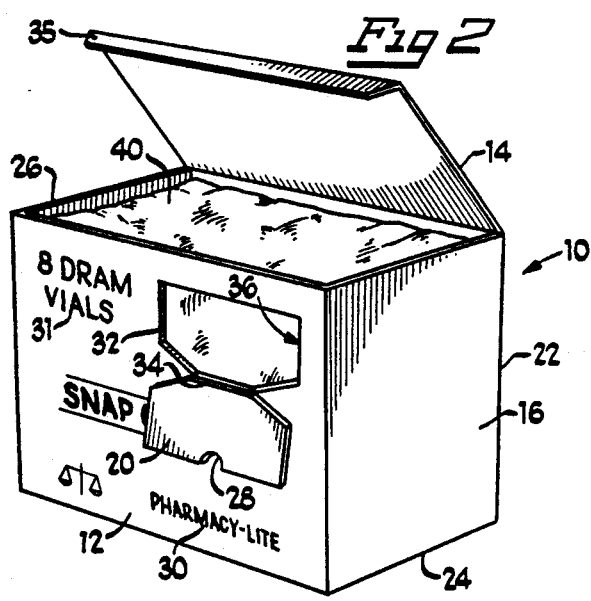
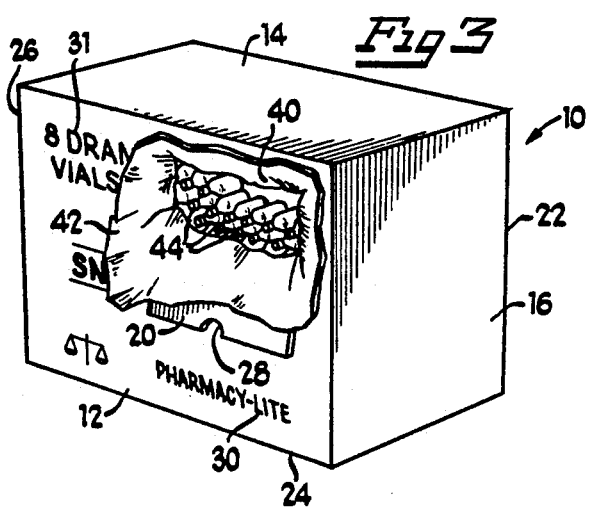
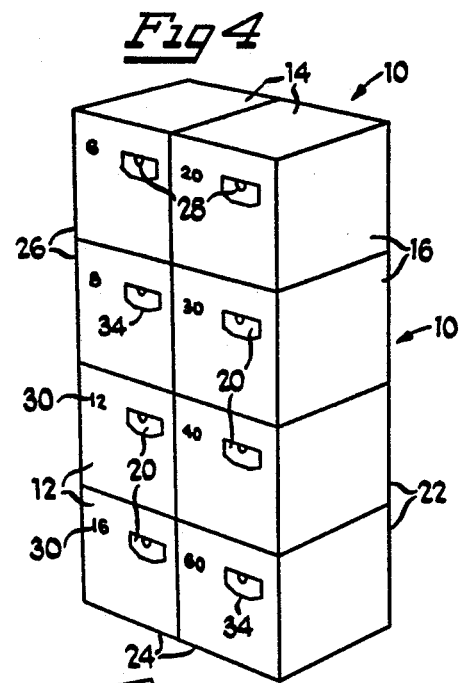
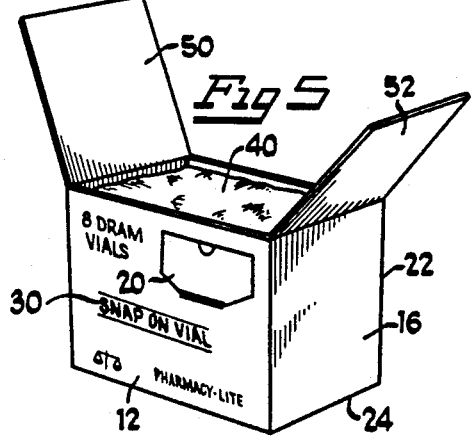
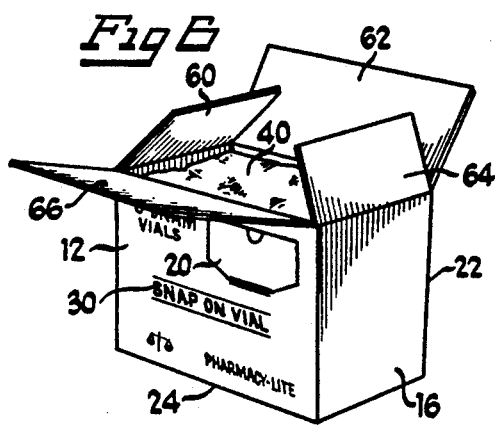

VIAL DISPENSING CARTON

BACKGROUND OF THE INVENTION

1. Field of the Invention

The present invention pertains to the storage, shipment, dispensing and inventorying of pharmaceutical vials. More particularly, the invention relates to cartons for storing and dispensing such vials, wherein each carton of a stacked array of cartons is specifically designed to be stacked with other cartons and to provide easy access to vials stored with the respective cartons.

2. Description of the Related Art

Presently, pharmaceutical vials, which often have a child-resistant closure, are purchased by pharmacies in bulk quantities in which one or more gross of vials are enclosed in a plastic bag. The vials come in various standard sizes and they are usually at least five to eight standard sizes for any given type of vial, e.g., a snap-type closure vial or a bayonet lock child-resistant closure. The pharmacy may have an inventory of various sizes and kinds of vials which are non-child resistant and simply have a screw-on or snap-on and off closure for those who do not like or have no need for child-resistant closures. Thus, it will be seen that a pharmacy may have in inventory a large number of open cartons or bags of vials of different kinds to store. Typically, small quantities of the different vials are taken from the bulk storage, plastic bags, e.g., in a back storage room and placed at a counter location more convenient to the pharmacist at the time of counting and placing pills in the vials.

The providing of a convenient and inexpensive way of storing a bulk inventory of these vials has not heretofore been accomplished. The cartons or plastic bags of vials may be piled on one upon another in the back room or expensive permanent shelving may be used with the plastic bags placed on the shelves. In any event, the size and shape of the storage area or facility is usually not tailored or customized to the size of the bulk plastic bags filled with vials to thereby minimize the overall volume of space for such storage and, at the same time, to provide an immediate visual indication of the array of vials of the respective sizes and types. There is a need for an improved and inexpensive system for inventorying and dispensing vials from bulk containers such as plastic bags.

In a number of instances, plastic bags of vials are shipped in paperboard cartons with top end flaps that are originally sealed and which are opened by the pharmacist and left open. Alternatively, these opened, top end flaps are "tucked in" and folded one within to the other to hold the individual flaps against being loose. The tucked in, end flaps result in an uneven top surface for the carton. Further, carton strength to support another carton or cartons of thereabove is diminished after the top end flaps are opened and vials are removed from this carton.

Accordingly, a general object of the invention is to provide a new and improved method of storing bulk vials and for dispensing the same.

A more specific object is to provide a stacking carton designed to serve several functions at once including packing, storing, shipping, inventorying and dispensing of the carton's contents.

SUMMARY OF THE INVENTION

In accordance with the present invention, an inventory of bulk vials are stored in a small volume space and are positioned to be easily accessed with the size and type of vial clearly designated. This is achieved by a stacked array of dispensing cartons each labeled with the particular style and size of vials stored therein. The preferred cartons are sized for the respective amount of vials to be stored therein at the time of bulk purchase of the vials. Typically, these vials are sold in bulk within cartons and plastic storage bags having one or more gross of vials in the bag. The preferred dispensing cartons are sized to these filled bags so that there is not an excessive empty volume in the stack of cartons. The druggist retrieves the vials from each carton by shifting an access panel, reaching in, and removing a handful of vials. The preferred access panel is movable between a closed position preventing dust from entering the carton and an open dispensing position at which the plastic bag may be positioned about the edges of the panel opening to prevent scraping of the hands or wrist.

Because the access panel is in the front wall of the carton, the tops of the carton remain unopened thereby providing a flat, even surface and strength to allow the cartons to be neatly stacked. Each of the stacked cartons will have an easy access window to reach in or to shake out vials. Thus, vials may be dispensed without the messy, open carton flaps of the prior art cartons.

BRIEF DESCRIPTION OF THE DRAWINGS

The invention will be described in connection with the accompanying drawings, in which:

FIG. 1 is a perspective view of a vial dispensing carton embodying and used in the present invention;

FIG. 2 is a perspective view thereof with the carton access panel in an open position and the carton top wall comprising a sealable flap in an open position revealing a plastic bag positioned within the carton;

FIG. 3 is a perspective view thereof with the carton access panel opened and portions of the plastic bag draped out from the face wall of the carton revealing vials stored within the plastic bag;

FIG. 4 is a perspective view of eight (8) vial dispensing cartons stacked in accordance with the present invention;

FIG. 5 is a perspective view of an alternative carton embodiment illustrating a top wall comprising two sealable flaps in accordance with the present invention; and FIG. 6 is a perspective view of an alternative carton embodiment illustrating a top wall comprising four sealable flaps in accordance with the present invention.

DETAILED DESCRIPTION OF THE PREFERRED EMBODIMENTS

As shown in the drawings for purposes of illustration, a large quantity of vials 42, e.g., one or more gross of vials, are stored in a plastic bag 40 (FIG. 3). These bags of vials were often merely placed in a heap in a storeroom or placed on storeroom shelves. When someone wanted a handful of vials, they went to the stored bags and sorted through them until they found the correct type of vial and the correct size of vial needed. The handful of vials were taken to the prescription counter area. In other instances, the vials were stored in cartons with top end flaps, which were originally sealed, and then torn open leaving a carton with messy, opened, top end flaps thereby making the cartons difficult to stack.

The storage of vials has been a generally haphazard and inefficient.

In accordance with the present invention, the bags of vials 40 are stored in dispensing cartons 10 which may be stacked in a neat and orderly array (FIG. 4). To obtain a handful of vials from a bag within a carton, a person will open a dispensing access flap or panel 20 in a wall 12 of the carton, thereby providing an easy access window to reach into the carton or from which window vials can be shaken out. Preferably, the access flap is a front wall 12 so that when the cartons are stacked in rows side-by-side and with back panels 22 against a wall, there is provided access to each plastic bag of vials. The preferred cartons have indicia thereon which designate the kind of vial, e.g., a snap-on vial, and also the size, e.g., 6, 8, 12, 16, 20, 30, 40 and 60 dram vial. The cartons are preferably stacked in size order and with all the vials of a given kind adjacent one another. Because the top end flaps of the cartons remain sealed, the tops of the cartons remain flat and even and very strong to support other cartons in a stacked array. Thus, the pharmacist can easily see all of the inventory of vials in a neat and small volume area.

The preferred and illustrated cartons 10 are made inexpensively, as for example, paperboard boxes with die cut openings to form the upper portion and sides of the access flap and a lower crease or fold to form a hinge 34 for pivotally connecting the access flap to swing between its closed position (FIG. 5) in the plane of the front wall 12, and its open position (FIGS. 2 and 3) in which it drops down below the hinge line 34. When a bag becomes empty, the pharmacist may either open the carton 10 by lifting a top side member 14 and replace the spent bag with a new full bag or throw out the old carton and bag and replace them with a new carton having a full bag of vials therein.

Turning now to a more detailed description of the invention, as illustrated in FIG. 1, the carton 10 has the front face wall 12 and the opposing back wall 22, the horizontal top member 14 and an opposing horizontal base member 24, and opposing sidewalls 16 and 26. The face wall 12 includes the access panel 20 which is die cut along three sides at a cutout edge 32 in the front wall 12. In a paperboard container, the access panel 20 is attached to the face wall 12 at the hinged portion 34 which is a creased fold line formed horizontally along the lower edge of the cutout. The hinged portion 34 allows the access panel 20 to be moveable between the closed storing position and the open dispensing position. In this preferred embodiment, the access panel is attached to the face wall 12 via hinged portion 34 which is integral with the face wall and the access panel 20. Alternatively, however, the access panel 20 could be composed of material different from that of the face wall 12 and attached at the hinged portion 34. In such an embodiment, hinged portion 34 includes separate attachment means to attach the access panel 20 to the face wall 12. In fact, it may be desirable to use an access panel 20 which is made from plastic or other transparent material to enable the user to check inventory without opening the access panel 20.

To facilitate opening and closing of the access panel 20, a small cutout portion, or finger hole 28, could be provided in the access panel 20 large enough to receive the end of a user's finger poked in the cutout portion when the user is moving the access panel 20 from its closed position to its opened position. The preferred finger hole 28 is located on the upper edge edge of the die cut panel opposite the hinged portion 34. As best seen in FIG. 1, the finger hole 28 is formed by the druggist punching out or pushing in a flat tab 28a of generally semi-circular shape, formed with a die cut so that either the tab 28a will break and separate from most of the remainder of the access panel and stay attached by a small hinge portion formed by a fold line or separate completely from the remainder of the access panel 20, thereby, in either event, leaving the finger hole 28.

Descriptive indicia 30 and 31 in the form of printing is provided on face wall 12 in order to facilitate use of the carton 10 as an inventorying and dispensing apparatus. Some descriptive indicia 31 is used to indicate the type and size of the contents of the carton 10. In the preferred embodiment wherein the carton 10 is utilized for the storage and dispensing of child-resistant pharmaceutical vials, the descriptive indicia 30 is used to indicate that the carton's contents are pharmaceutical products for prescription packaging, and designate the kind of vials therein, e.g., snap-cap vials. In addition, the vial sizes are indicated in drams by the indicia 31 on the carton. Typically 6, 8, 12, 16, 20, 30, 40 and 60 dram sizes are provided in the preferred embodiment.

Turning to FIG. 2, the access panel 20 is shown in its open position, thus revealing a window opening 36 defined by cutout edge 32. The contents of the carton 10 are revealed through the window opening 36. As illustrated, the access panel 20 is movable between the closed position shown in FIG. 1 and the open position shown in FIG. 2.

Returning now to the preferred embodiment, as stated above and as shown in FIG. 2, the access panel 20 and face wall 12 are composed of the same material and hinged at hinged portion 34. The top member 14 may comprise (as shown in FIG. 2) a single sealable flap, having a lip portion 35 receivable at the top of face wall 12 of the carton 10. The top member 14 comprising a sealable flap, allows a bag of vials to be placed within the carton 14 when it is in an open position, as illustrated in FIG. 2. The flap 14 provides a flat, even surface to support another carton on the top thereof to form a stack of cartons. FIG. 2 shows contents within the carton 10, namely plastic bag 40 and the pharmaceutical vials stored herein, in accordance with the preferred embodiment of the invention.

As best seen in FIG. 3, the carton 10 has the access panel 20 in the open position with loose plastic bag portions at plastic bag edges 42 draped about the cutout edge 32 to cover any sharp die cut edges to prevent injury to a hand or wrist inserted through the window opening 36. Advantageously, when the carton 10 is in the opened dispensing position as illustrated in FIG. 3, the opening providing access to the vials 44 is large enough to allow a human hand to enter the carton 10. Thus, the draping of the plastic bag 40 at edges 42 facilitates the use of the carton 10 as a dispensing apparatus, because the plastic bag prevents the scraping of one's hand on cutout edge 32, as the hand is inserted or removed from the carton 10.

The carton 10 as illustrated in FIGS. 1, 2 and 3 could be made of a wide variety of materials other than the preferred paperboard, e.g., including plastics, metal, wood etc. However, in accordance with the preferred embodiment, it would be advantageous to construct the carton 10 from inexpensive, die cut cardboard or paperboard box material, making it a convenient and disposable apparatus for packing, storage, shipping, inventorying and dispensing.

Multiple uses for a disposable carton is a key aspect of the present invention, especially when used for containing pharmaceutical items in accordance with the preferred embodiment. There are a number of significant advantages associated with the carton 10. The multiple purposes associated with the carton 10 is a source of significant labor savings. In particular, there is no need to ever unpack the contents of the carton 10. Ideally, once the contents are packaged and permanently sealed in the carton 10, the end-user druggist need not remove the contents by opening the horizontal top member 14, but rather utilizes the carton 10 as a dispenser removing items as needed by moving the access panel 20 to its opened dispensing position draping the plastic bag edges 42 from the window opening 36 and reaching into the carton 10 to retrieve items by hand.

Moving the access panel 20 to an open position also allows the end-user to determine whether the inventory is depleted without having to open the horizontal top member 14. As a by-product of the reduced labor associated with unpacking, inventorying and dispensing, the minimal handling associated with these activities lessens the likelihood that the items contained in carton 10 will be exposed to dirt or dust, thus providing a much cleaner storage environment. Since the vials 44 are kept at all times within the plastic bag 40, their exposure to airborne and other contaminants is far less than their exposure would be if left in open cartons or unpacked and placed on an open air shelf or rack at the end-user's place of business.

Since, in the preferred embodiment, like items (vials 44) are intended to be stored within the carton 10 and identified by descriptive indicia 30, there is less likelihood of one mixing up the items with other items having different sizes or character. This reduced likelihood for mixing of inventory is achieved through the design of the carton 10 itself, as illustrated in FIGS. 1-3, as well as the reduced need for handling items contained in the carton 10.

Turning now to FIG. 4, as illustrated, eight (8) cartons 10 are stacked in an array. Since the carton 10 is stackable with like cartons, the carton 10 is easily incorporated into the end-user's inventory system, thus also removing the need for a special fixtures at the end-user's place of business. When utilized as shown in FIG. 4, the cartons 10 cooperating with one another by being stacked upon or adjacent to similar cartons 10, the result is a convenient inventory and dispensing fixture for different sizes or different character of items. The top of the cartons remain flat and even to facilitate the stacking of another carton on top of the bottom carton. Once an item is depleted, the end-user druggist simply removes the empty carton 10 and disposes of it, replacing it with another carton 10 added to the stack to replenish the supply of the vials 44. Alternatively, a new bag of closures could be placed in the empty carton and the carton may be used for a number of times with different bags of vials.

The above-described inventory structure utilizing cartons 10, which are disposable, is also a source of significant space, labor and costs savings to the end-user.

Referring now to FIGS. 5 and 6, alternative embodiments of the carton 10 are illustrated to show the horizontal top member 14 comprising plural, sealable flaps 50, 52, 60, 62, 64 and 66. In the prior art cartons, access to the interior of the cartons was achieved by pulling open these top sealed flaps and then the flaps were either left open or they were tucked into each other. In addition to the potential for plural sealable flaps to comprise a wall of the carton 10, depending upon the preference of the manufacturer or shipper of items contained therein, it would also be possible to incorporate such sealable flaps into any of the other walls which comprise the carton 10, including the pair of sidewalls 16 and 26, the back wall 22 or even the horizontal base member 24 or the face wall 12. Such embodiments are considered to be consistent with the character and nature of the present invention.

From the foregoing, it will be seen that the present invention provides a new and improved method of storing an inventory of vials in dispensing cartons which are stackable and which have indicia thereon indicating the type and size of vial in each carton. Preferably, the cartons are sized to receive and hold a standard plastic bag of vials; and an access flap in a front face of each carton of the stack allows a person to reach in and extract a handful of vials from a container. The preferred containers are made of inexpensive paperboard or plastic with an integral hinge line for hinging the access flap to pivot between its open dispensing position and its closed position. The top ends of the cartons remain flat, unopened and strong even though vials have been removed from the container. To protect the user's hands from scratches or scrapes along die cut edges of the access window, the mouth of the plastic bag may be pulled outward from inside the carton and draped over the die cut edges.

The drawings and the foregoing descriptions are not intended to represent the only forms of the invention in regard to the details of its construction and manner of operation. Changes in form and in the proportion of parts as well as the substitution of equivalents are contemplated as circumstances may suggest or render expedient and although specific terms have been employed, they are not intended in a generic and descriptive sense only and not for the purposes of limitation, the scope of the invention being delineated by the following claims.

What is claimed is:

1. A carton for dispensing items contained therein, said apparatus comprising:
    a horizontal base member;
    a pair of side sidewalls attached tot he base member extending vertically from said base member;
    a back sidewall attached to the base member and the sidewalls extending vertically from said base member;
    a face sidewall attached to the base member and the sidewalls extending vertically from said base member;
    a horizontal top member attached to said face, back and sidewalls and remaining in a flat, horizontal, closed position when items are being dispensed;
    a plastic bag positioned between in a hollow interior, defined within said members and sidewalls, the plastic bag holding said items therein;
    a fold line means between the horizontal top member and at least one of said sidewalls to allow pivoting of the top member from an open position to allow insertion of the plastic bag full of the items into the carton prior to pivoting the horizontal base member to its closed position;
    an access panel integral with and in the face sidewall and movable between a closed position closing an access opening into the interior of the carton, and an open dispensing position allowing the insertion of a human hand to retrieve the items from the interior of the carton; and neck portions of the plastic bag being pulled through the opening in the face sidewall and draped about the opening in the face sidewall when the access panel is in the open dispensing position, while the top member is in its closed position, to allow insertion of a hand to retrieve the items in the plastic bag.

2. The carton of claim 1 wherein descriptive indicia relating to the items in the carton is placed on said face sidewall.

3. The carton of claim 1 wherein said access panel is cut out from the face sidewall of the carton.

4. The carton of claim 1 wherein a hinged connection joins the access panel to the face sidewall of the carton.

5. The carton of claim 1 wherein said access panel further comprises means for grasping on the access panel allowing a human hand to grasp and move the access panel between the closed storage position and the open dispensing position.

6. The carton of claim 1 wherein said top member further comprises a sealable flap allowing items to be placed into the carton and permanently sealed therein to remain sealed while the only access into the carton interior is through the access panel.

7. The carton of claim 1 wherein said back wall further comprises a sealable flap allowing items to be placed into the carton and permanently sealed therein.

8. The carton of claim 1 wherein said face wall further comprises a sealable flap allowing items to be placed into the carton and permanently sealed therein.

9. The carton of claim 1 wherein said base member and said top member have flat, even surfaces allowing the carton to be stacked upon another carton.

10. The carton of claim 1 wherein the items contained in the carton are pharmaceutical child-resistant vials.

11. The carton of claim 11 wherein descriptive indicia relating to the size of the vials contained in the carton, allowing the carton to be utilized as a dispenser of said vials.

12. A method of dispensing items stored in plastic bags within sealed cartons, each carton having top, bottom, side, back and face panels, each face panel further having an access panel and descriptive indica relating to the size and identification of the items, the method comprising the steps of:

providing a plurality of said cartons each with a flat, top panel;

stacking each said carton in a predetermined order as to the size and identification of the items stored within the cartons;

moving the access panel to an open dispensing position thereby leaving an access window;

pulling a neck of the plastic bag outwardly through the access window to drape out from the resulting access window in the face panel when the access panel is in the dispensing position;

inserting a human hand through said access window into said plastic bag to retrieve the items contained therein, the draped portion of the plastic bag preventing the human hand from being scraped;

moving the access panel to a closed position in which airborne contamination is prevented from coming in contact with the items.

13. A structure for storing and dispensing various sized vials and closures, said structure comprising:

a plurality of cartons stacked vertically and adjacent one another arranged by size order, each carton having size and identification indicia on it;

each of said cartons being stacked and supported on one another and having a face sidewall exposed without a supporting carton covering the face sidewall;

said cartons each comprising:

a horizontal base member;

a pair of sidewalls attached to the base member extending vertically from said base member;

a back sidewall attached to the base member and the sidewalls extending vertically from said base member;

a face sidewall attached to the base member and the sidewalls extending vertically from said base member;

a horizontal top member attached to said face, back and sidewalls;

a plastic bag positioned between said face, back and sidewalls and positioned between said top and bottom members, the plastic bag holding the vials and closures therein;

said face sidewall having an access panel integral therewith and pivotable about a fold line between a closed position preventing airborne contamination from coming in contact with the vials and closures and an open dispensing position allowing the insertion of a human hand to retrieve the vials and closures and;

descriptive indicia relating tot he items in the carton on the face sidewall and exposed to the person who desires to retrieve the described vials and closures therein.

* * * * *